United States Patent
Gill et al.

(10) Patent No.: US 10,011,662 B2
(45) Date of Patent: Jul. 3, 2018

(54) DOWNSTREAM PROCESS FOR PURIFYING POLYSACCHARIDES

(71) Applicant: MSD WELLCOME TRUST HILLEMAN LABORATORIES PVT. LTD., New Delhi (IN)

(72) Inventors: Davinder Gill, New Delhi (IN); Manoj Kumar Chhikara, Delhi (IN); Sandeep Sharma, Uttar Pradesh (IN); Sarmad Hanif, New Delphi (IN); Neeraj Joshi, New Delhi (IN)

(73) Assignee: MSD WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 13 days.

(21) Appl. No.: 15/119,847

(22) PCT Filed: Feb. 24, 2015

(86) PCT No.: PCT/IB2015/051371
§ 371 (c)(1),
(2) Date: Aug. 18, 2016

(87) PCT Pub. No.: WO2015/128798
PCT Pub. Date: Sep. 3, 2015

(65) Prior Publication Data
US 2017/0051080 A1 Feb. 23, 2017

(30) Foreign Application Priority Data
Feb. 25, 2014 (IN) .............................. 527/DEL/2014

(51) Int. Cl.
*C08B 37/00* (2006.01)
*C12R 1/36* (2006.01)
*B01D 15/32* (2006.01)
*B01D 21/26* (2006.01)
*B01D 61/14* (2006.01)

(52) U.S. Cl.
CPC ........ *C08B 37/0003* (2013.01); *B01D 15/327* (2013.01); *B01D 21/262* (2013.01); *B01D 61/145* (2013.01); *C08B 37/0006* (2013.01); *C12R 1/36* (2013.01)

(58) Field of Classification Search
None
See application file for complete search history.

(56) References Cited

U.S. PATENT DOCUMENTS

| | | | |
|---|---|---|---|
| 6,248,570 B1 * | 6/2001 | Michon | .................. C08B 37/00 424/234.1 |
| 8,398,985 B2 * | 3/2013 | Kapre | ................. C08B 37/0003 424/184.1 |
| 2007/0154492 A1 | 7/2007 | Michon et al. | |

FOREIGN PATENT DOCUMENTS

| WO | WO94/05325 | * | 3/1994 |
| WO | 2005024038 A2 | | 3/2005 |

OTHER PUBLICATIONS

Jennings et al., "Induction of Meningococcal Group B Polysaccharide-Specific IgG Antibodies in Mice by Using an N-Propionylated B Polysaccharide-Tetanus Toxoid Conjugate Vaccine" Journal of Immunology (1986) vol. 137 pp. 1708-1713 (Year: 1986).*
Thermo Scientific(R) "Convert between times gravity (xg) and centrifuge rotor speed (RPM)" (C)2009 Thermo Ficher Scientific Inc, downloaded from www.thermo.com/pierce (Year: 2009).*
Pato T P et al; "Purification of Capsular Polysaccharide from Neisseria Meningitidis Serogroup C by Liquid Chromatography", Journal of Chromatography B: Biomedical Sciences & Applications, Elsevier, Amsterdam, NL, vol. 832, No. 2, Mar. 7, 2006, pp. 262-267.

* cited by examiner

*Primary Examiner* — Eric Olson
(74) *Attorney, Agent, or Firm* — W&C Intellectual Property

(57) ABSTRACT

The present invention relates to a novel process for purifying bacterial polysaccharide. It is an efficient and scalable process for removing impurities from *Neisseria meningitidis* serogroup C (Men-C) polysaccharide which is capable of being used as such in a derivatized form or linked to other molecules, for the preparation of vaccines, more particularly conjugate vaccines for *N. meningitidis* infection.

7 Claims, 2 Drawing Sheets

DOWNSTREAM PROCESS FOR PURIFYING POLYSACCHARIDES

FIELD OF THE INVENTION

The present invention relates to a rapid process for purifying *Neisseria meningitidis* polysaccharide. More specifically, the present invention relates to a process of preparing *N. meningitidis* serogroup type C (MenC) polysaccharides capable of being used as such, or of being derivatized or combination to other serogroups to make vaccines for *N. meningitidis.*

BACKGROUND OF THE INVENTION

Polysaccharides, especially antigenic polysaccharides, are used in preparation of vaccines. Monovalent, bivalent and poly (multi) valent vaccines containing one, two or more polysaccharides and their conjugates are available in the market for prevention of certain diseases or infections caused by various microorganisms such as *Streptococcus pneumoniae, Haemophilus influenzae* and *N. meningitidis* and have proved valuable in preventing the respective diseases to a significant extent. Surveillance data gathered in the years following the introduction of the vaccine Prevenar has clearly demonstrated a reduction of invasive pneumococcal disease in US infants as expected. Despite of several studies carried out on these polysaccharides and conjugates, a need for improving yields as well as quality (purity) of the polysaccharides always exist in the industry as evidenced by the continuing research.

Meningitis is considered as a global threat and the disease burden still remains a public health priority. The clinical definition of meningitis is the inflammation of the meninges (membrane of the brain). If not treated, the disease can have fatal consequences. A total of thirteen serogroups of *N. meningitidis* have been identified, and out of these thirteen, six serogroups (A, B, C, W135, X and Y) are majorly accountable for causing the infections globally. *N. meningitidis* has a wide range of clinical manifestations, ranging from transient mild sore throat to fatal meningitis or meningococcal septicemia. Meningitis and septicemia are the most common presentations of the disease.

Evidence collected through numerous research findings defines the immunogenic aspect of the polysaccharide conjugate vaccine. Furthermore, there are research articles as well as patents describing the production and purification of the capsular polysaccharide of Men C but none of them define a purification process with extremely reduced time lines which is robust, scalable, and reproducible.

The production of purified Men C is the foremost requirement for an effective conjugation with the carrier protein and its development as a conjugate vaccine. The cost for the cultivation and the purification of Men C is generally high and involves long working hours as it involves a series of production and purification steps. Improvement in one or more of the steps of polysaccharide production would bring a significant change in the overall conjugate vaccine production and consequently makes the process relatively cost effective.

However, despite of several studies that have been carried out on these polysaccharides, there has always been a need for improving yields as well as quality/purity of the polysaccharides in order to produce vaccines of high quality.

There are a number of patents, which describe the process for the purification of Men-C polysaccharides. The existing state of the art described in U.S. Pat. No. 7,491,517,B2 for precipitating Men-C polysaccharides with CTAB is found to involve overnight incubation at 4° C. Also the removal of contaminants requires the use of costly enzyme Proteinase K. In addition to this, the process also requires gel filtration for the purification of the Men-C polysaccharides. The overall procedure requires significant time for purification and also the process becomes costly because of the use of enzymes.

Also, the Application No. WO 2011/148382 A1 describes the method of preparing pure capsular polysaccharide using aluminium phosphate with alcohol for the purification of capsular polysaccharides of *Haemophilus influenzae* b, *N. meningitidis* such as serogroups A, C, Y, W-135 and other similar capsular polysaccharides produced form both gram negative and gram positive microorganisms. The said published prior art discloses a time of 16-20 hrs for the purification of the polysaccharides.

Another patent EP 0658118B1 describes a method for O-Deacetylation of Group C Meningococcal Polysaccharide (GCMP) with an average time of 16 hours. This process also requires significant time for purification Presently, the various methods used for the production and purification of MenC polysaccharides takes relatively long cultivation and purification time and also involves the use of costly enzymes. Though these kinds of processes give pure polysaccharides but they will concurrently increase the cost of production during scale-up.

Furthermore the above disclosed prior arts teach methods which are more efficient at low temperature thereby requiring a controlled environment leading to addition of costs in research and production.

OBJECT OF THE INVENTION

Thus the main object of the present invention is to provide a novel process for the purification of Men C polysaccharide.

Another object of the invention is to provide a rapid process for purification of Men C polysaccharide while eliminating the impurities in a very short time by simple, efficient, improved and commercially scalable method.

Yet another object of the present invention is to produce high quality polysaccharide which meet the relevant WHO specifications.

SUMMARY OF THE INVENTION

The present invention relates to the process for purification of Men C polysaccharide. The process describes a novel, rapid, cost effective, and scalable method, wherein Men C polysaccharide is purified with significantly reduced time.

The process of the instant invention involves the selection of immunologically active bacterial strain, preparing the media for the propagation of said immunologically active strain and inoculating the selected bacterial strain in glycerol stock culture and incubating it at predefined temperature for an optimal time period at predefined revolutions per minute (rpm). The selected bacterial strain is cultivated on optimized cultivation media in the fermenter and the process proceeds by doing the centrifugation of the fermented harvest to clarify the fermentation broth (FB) of cell debris followed by concentration of the FB by ultrafiltration using molecular weight cut-off membranes.

The ultra-filtered concentrated supernatant or the processed FB is then deacetylated in presence of high concentration of alkaline solution at high temperature. The deacetylated crude polysaccharide is subjected to buffer exchange through Tangential Flow Filtration (TFF). Diafiltered deacetylated crude polysaccharide is further purified by hydrophobic interaction chromatography (HIC) followed by diafiltration and concentration to get the final purified polysaccharide. Of particular relevance is the method according to the invention which comprises the treatment of a concentrated extract and/or isolated bacterial cells with a basic solution. In addition to extracting the CPS, the base extraction also causes deacetylation of N-acetyl groups. The extent of the deacetylation may be varied by adjusting the reaction conditions. The extracted CPS are then separated from the cellular components to obtain the CPS preferably by chromatographic separation.

The process exhibits a number of advantages over prior art, such as providing a novel and rapid method of preparing Men C polysaccharide. The process is cost effective as it reduces the total number of steps and requires single chromatographic screening. An additional advantage is that this process is entirely scalable.

DETAILED DESCRIPTION OF THE INVENTION

Figure 1:
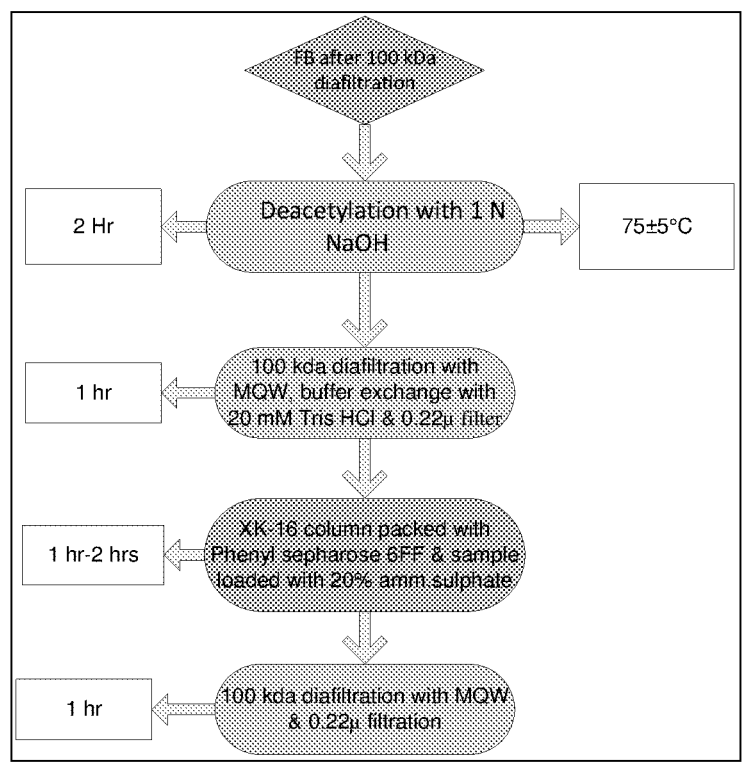
FIG. 1 Depicts the process flow for the MenC-PS purification and recovery.

The invention discloses two steps that have been optimized to enable the purification of MenC polysaccharide (MenC-PS) in lesser time as shown in FIG. 1.

The strain of bacterial polysaccharide is inoculated in the fermenter containing appropriate media components required for bacterial growth. After achieving the maximum optical density, in the range of 8 to 10 depicting substantial bacterial growth, it is subjected to termination by adding prerequisite concentration of formaldehyde and the resultant FB is obtained. FB is then centrifuged at high speed to clarify the FB of cell debris followed by diafiltration and concentration using molecular weight cut-off membranes.

The diafiltered and concentrated FB having the crude polysaccharide is treated with NaOH at high temperature e.g up to 80° C. for deacetylation. Concentration and diafiltration of the crude polysaccharide is performed with polyether sulfone (PES) membrane, with milliQ water (MQW), followed by Tris HCl buffer pH 7.4±0.1. After diafiltration crude polysaccharide is concentrated and filtered with 0.22 µm filter.

Deacetylated crude polysaccharide is further purified by Hydrophobic interaction chromatographic (HIC) technique.

The separation of two or more components of a mixture based on differences in polarity is well known to those skilled in the art. For example, using hydrophobic-interaction chromatography, compounds of relatively greater hydrophobicity are retained longer on the column relative to those compounds that are more hydrophilic. Conversely, using hydrophilic-interaction chromatography, hydrophilic compounds are retained longer on the column relative to those compounds that are more hydrophobic. Using both methods consecutively allows for the removal of impurities that are both less polar and more polar relative to the compound of interest The extracted CPS present in the base extraction reagent can be separated from impurities resulting from the cellular components by chromatography. Non-limiting examples of the chromatographic separation methods are ion-exchange (cationic or anionic), hydrophilic-interaction, hydrophobic-interaction or gel-permeation chromatography. More preferred is hydrophobic-interaction chromatography (HIC) on phenyl sepharose which will remove most of the high molecular weight, uv-active contaminants from the base extract. Capsular polysaccharide will elute in the beginning, while, the more hydrophobic protein and nucleic acids will be retained. The preferred method in this invention is hydrophobic-interaction chromatography.

Further concentration and diafiltration of the polysaccharide is performed to facilitate the removal of proteins and other impurities, and the polysaccharide sample is then washed with MQW.

Figure 2:
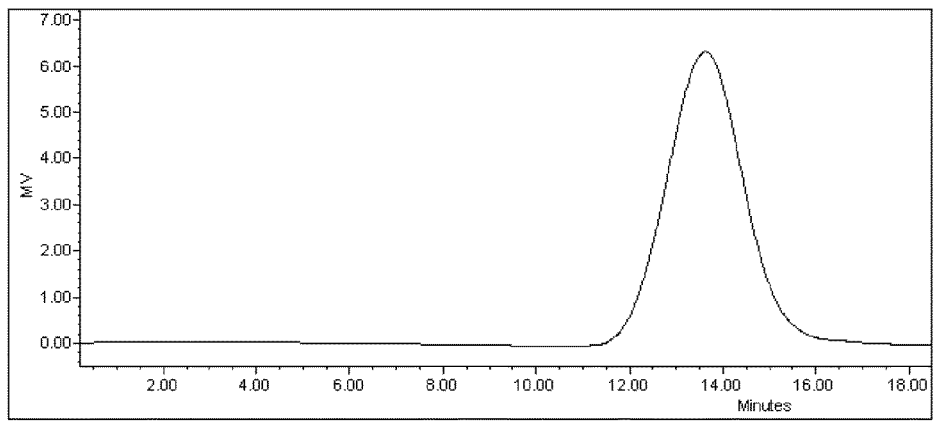
FIG. 2 Depicts the HPLC Chromatogram of MenC-PS
FIG. 3 Depicts the NMR spectrum of MenC-PS.
Figure 3:
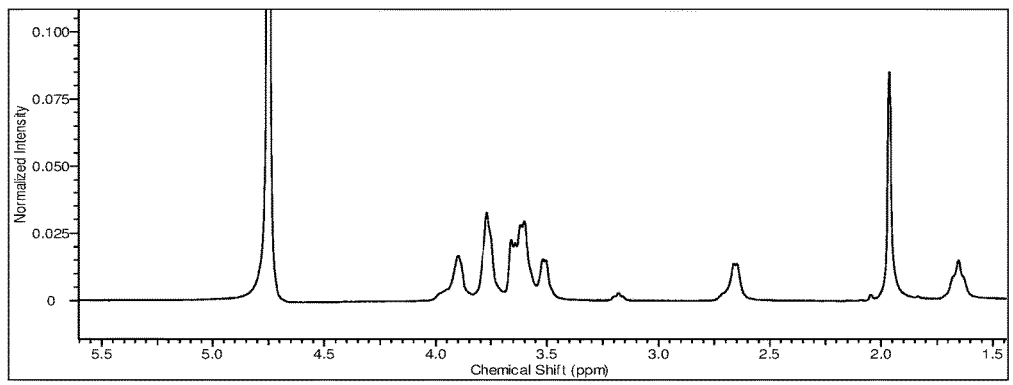

Consequently sterile filtration is done to obtain the purified Men C polysaccharide depicted by FIGS. 2 and 3.

The corroboration of the above employed procedures can be conveniently understood from Table 1 which clearly shows that the purified polysaccharide specifications meet the WHO standard.

TABLE 1

Purified Men-C polysaccharide specifications in accordance with WHO specification are shown below

| Tests | MenC-PS | WHO Specifications |
|---|---|---|
| Polysaccharide content | 4 mg/ml | Actual value |
| Sialic acid content | 100% | The sialic acid for MenC content not less than 80% of the dry weight |
| Endotoxin | <0.06 EU/µg | Less than 100 EU/µg |
| Protein % | 0.14% | Not more than 1% |
| Nucleic Acid % | 0.42% | Not more than 1% |
| Average relative Molecular Weight | 351 kd | Actual value from HPLC |
| Identity | Positive | Positive agglutination reaction with specific sera; Defined $^1$H-NMR spectrum |

Of particular interest is the observation that the time required to purify the Men C polysaccharides is significantly less from those disclosed in the prior arts whereas the hallmark of the present invention is the novel, rapid and scalable purification process protocol which can be completed within 6±1 hours and the PS so produced is in compliance with the WHO set standard.

Analytical Procedures:

Polysaccharide obtained at different steps are constantly monitored and analyzed for their purity and yield. Different analytical procedures are reported but the preferred ones are as summarized below:

Total sialic acid of MenC-PS is determined by a colorimetric method. The assay is based on the reaction between sialic acid and resorcinol at 100° C. in the presence of hydrochloric acid and copper (II) ions for 30 minutes; this leads to the formation of a blue-violet complex which exhibits a strong absorbance at 564 nm. The total sialic acid concentration is determined from a calibration curve obtained using a series of sialic acid standards [(Svennerholm, 1957)]. Lipopolysaccharide (LPS) is determined using compact and simple Endosafe®-PTS™ apparatus. Protein impurity is determined by Lowry's method [(Lowry et al., 1951)] using bovine serum albumin as a standard and the absorbance is taken at 750 nm. Nucleic acids (NA) is estimated at 260 nm and the amount is calculated assuming an absorbance of 1.0 A=50 µg/mL [(Frasch, 1990)].

Relative Average molecular size (Mw) of HibPRP is determined using High-performance liquid chromatography (HPLC) (Alliance, Waters). The columns used are PWXL-4000 and PWXL-5000 in series (Tosoh Bioscience). Furthermore, a range of 5 kD to 800 kD Pullulans (Shodex) are used as standards for MenC-PS. The HPLC is performed using 0.1 M sodium nitrate with a run time of 30 min at a flow rate of 1 ml/min. The identity of MenC-PS is verified by 1H-NMR spectroscopy. NMR yields a spectrum of magnetic sensitive nuclei (e. g. 1H).

The MenC-PS is identified serologically by combining with the reference antisera against each polysaccharide. As the WHO specifications [WHO, 2004] to determine the purity and to characterize the polysaccharide is based on dry weight basis, the MenC-PS is first lyophilized and then tested. The moisture content is thus subtracted to get the exact dry weight. Moisture content of lyophilized cake is determined by Thermo gravimetric Analyzer (TGA) from Perkin Elmer. The analytical results for MenC-PS are given in Table-1 and are in accordance and as specified by WHO.

The said Men C polysaccharide can be used for the preparation of polysaccharide-protein conjugate vaccines.

Various aspects of the invention described in details above is now illustrated with non-limiting examples.

EXAMPLE-1

Polysaccharide Purification Using Anionic Detergent with Tris Buffer and Hydrophobic Interaction Chromatography (HIC):

The diafiltered and concentrated FB having the crude polysaccharide is processed with anionic detergent, such as, sodium deoxycholate at a concentration 0.3% to 0.6% (w/v) and incubated at 50° C.-60° C. for 1 hour. Subsequently it is cooled to below 40° C. followed by concentration and diafiltration of the crude polysaccharide with 0.1 m$^2$ poly ether sulfone (PES) membrane, with 6-8 volumes of milliQ water (MQW).

Deacetylation is then performed on the crude polysaccharide with 0.5M sodium hydroxide (NaOH) at 50° C. for 10 hours. Subsequently it is cooled to below 40° C. followed by diafiltration and concentration of the crude polysaccharide simultaneously with 6-8 volumes of MQW and 20 mM Tris HCL buffer using 0.1 m$^2$ PES membrane. Afterwards the polysaccharide is further purified by Hydrophobic Infraction Chromatography (HIC), Such as, Phenyl sepharose 6 Fast Flow. Finally, concentration and diafiltration of the purified polysaccharide was performed with 0.1 m$^2$ PES membrane, with 6 to 8 volumes of MQW. Accordingly, sterile filtration is done with 0.22 μm filter and the final purified polysaccharide is stored at −20° C. The total time taken to purify the polysaccharide including HIC chromatography using the above process was 16-18 hours.

EXAMPLE-2

Polysaccharide Purification Using Anionic Detergent with HEPES Buffer (4-(2-Hydroxyethyl)-1-Piperazineethanesulfonic Acid) and Hydrophobic Interaction Chromatography (HIC):

The diafiltered and concentrated FB having the crude polysaccharide is processed with anionic detergent, for example, sodium deoxycholate at a concentration 0.3% to 0.6% (w/v) and incubated at 50° C.-60° C. for 1 hour. Subsequently it is cooled to below 40° C. followed by concentration and diafiltration of the crude polysaccharide with 0.1 m$^2$ poly ether sulfone (PES) membrane, with 6-8 volumes of MQW.

Deacetylation is then performed on the crude polysaccharide with 0.5M sodium hydroxide (NaOH) at 50° C. for 10 hours. Subsequently it is cooled to below 40° C. followed by diafiltration and concentration of the crude polysaccharide simultaneously with 6-8 volumes of MQW and 20 mM HEPES containing 3M NaCl buffer using 0.1 m$^2$ PES membrane. Afterwards the polysaccharide is further purified by Hydrophobic Interaction Chromatography (HIC), Such as, Phenyl sepharose 6 Fast Flow. Concentration and diafiltration of the purified polysaccharide was performed with 0.1 m$^2$ PES membrane, with 6-8 volumes of MQW. Consequently, sterile filtration was done with 0.22 μm filter and the final purified polysaccharide is stored at −20° C. The total time taken to purify the polysaccharide including HIC chromatography using the above process was 16-18 hours.

EXAMPLE-3

Polysaccharide Purification Using Sodium Hydroxide with HEPES Buffer ((4-(2-Hydroxyethyl)-1-Piperazineethanesulfonic Acid) and Hydrophobic Interaction Chromatography (HIC):

The diafiltered and concentrated FB having the crude polysaccharide is deacetylated with 0.8M NaOH for 6 hours at 80° C. Subsequently it is cooled to below 40° C. followed by diafiltration and concentration of the crude polysaccharide simultaneously with 6-8 volumes of MQW and 20 mM HEPES containing 3M NaCl buffer using 0.1 m$^2$ PES membrane. Afterwards the polysaccharide is further purified by Hydrophobic Interaction Chromatography (HIC), Such as, Phenyl sepharose 6 Fast Flow. Concentration and diafiltration of the purified polysaccharide was performed with 0.1 m$^2$ PES membrane, with 6-8 volumes of MQW. Consequently, sterile filtration was done with 0.22 μm filter and the final purified polysaccharide is stored at −20° C. The total time taken to purify the polysaccharide including HIC chromatography using the above process was 10-12 hrs. Moreover the polysaccharide is partially purified with the above mentioned process. The process may require few more steps for complete purification of the polysaccharide and may not be a cost effective process.

EXAMPLE-4

Polysaccharide Purification Using Sodium Hydroxide with Tris Buffer and Hydrophobic Interaction Chromatography (HIC):

The diafiltered and concentrated FB having the crude polysaccharide is deacetylated with 0.8M NaOH for 6 hours at 80° C. Subsequently it is cooled to below 40° C. followed by diafiltration and concentration of the crude polysaccharide is done simultaneously with 6-8 vols of MQW and 20 mM Tris HCL buffer using 0.1 m$^2$ PES membrane. Afterwards the polysaccharide is further purified by Hydrophobic Infraction Chromatography (HIC), Such as, Phenyl sepharose 6 Fast Flow. Concentration and diafiltration of the purified polysaccharide was performed with 0.1 m$^2$ PES membrane, with 6 to 8 volumes of MQW. Accordingly, sterile filtration is done with 0.22 μm filter and the final purified polysaccharide is stored at −20° C. The total time taken to purify the polysaccharide including HIC chromatography using the above process is 10-12 hours. Moreover the polysaccharide is partially purified with the above mentioned process. The process may require few more steps for complete purification of the polysaccharide and may not be a cost effective process.

EXAMPLE-5

Polysaccharide Purification Using Sodium Hydroxide with Tris Buffer and Hydrophobic Interaction Chromatography (HIC):

The diafiltered and concentrated FB having the crude polysaccharide was deacetylated with 1M NaOH for 2 hrs at 75±5° C. The deacetylated polysaccharide was then cooled to a temperature below 40° C. After cooling, the concentration and diafiltration of the crude deacetylated polysaccharide was performed through 100 KDa PES membrane (0.1 m$^2$) with 20 to 25 volumes of MQW, followed by 8-10 volumes of 20 mM Tris HCl buffer (pH 7.4±0.1). Consequently sterile filtration was done with 0.22 μm PES membrane (0.1 m$^2$).

Daifiltered deacetylated polysaccharide was further purified by hydrophobic interaction chromatrography (HIC) through XK-16 column packed with phenyl sepharose 6 fast Flow (FF) using chromatography system. The column was equilibrated with 20 mM Tris HCl buffer pH 7.4±0.1 containing 20% Ammonium Sulphate. The material was loaded at 60 cm/hr. and the flow through containing the purified polysaccharide was collected. Finally column was regenerated with 20 mM Tris HCl buffer pH 7.4±0 and stored in 20% ethanol for further use. Concentration and diafiltration of the purified polysaccharide was performed with 100 KDa PES membrane (0.1 m$^2$), with 6-8 volumes of MQW and sterile filtration is done with 0.22 μm filter and the final purified polysaccharide is stored at −20° C. The total time taken to purify the polysaccharide is 6±1 hours and the PS qualifies to the WHO specifications.

We Claim:

1. A process for purifying Men C-Polysaccharide, wherein said process comprises the steps of:
   (a) centrifugation of the fermented harvest to clarify the fermented broth;
   (b) concentrating the fermented supernatant by ultrafiltration;
   (c) deacetylation and incubating said concentrated supernatant of step (b) at a temperature ranging from 70° C. to 80° C.;
   (d) collecting the supernatant of step (c) and subjecting to diafiltration and concentration;
   (e) purification of diafiltered supernatant of step (d) by chromatography;
   (f) diafiltration and concentration to obtain purified polysaccharides; and
   (g) sterile filtration of said purified polysaccharides,
   wherein the said purification process is completed within 6±1 hours and wherein the purification process is completed without the use of a detergent.

2. The process as claimed in claim 1 wherein said step of centrifugation of the fermented harvest is carried at 4500×g to 5000×g.

3. The process as claimed in claim 1 wherein said step of deacetylation is carried with NaOH solution at a concentration which ranges from 1 to 1.5 M.

4. The process as claimed in claim 1 wherein the incubation in the deacetylation step is performed with a total incubation time ranging from 1 hour 30 mins to 2 hours 30 min.

5. The process as claimed in claim 1 wherein the diafiltration in the collecting step after the deacetylation step is carried out 20 to 25 times with Milli-Q water followed by 8 to 10 times with 25 mM Tris HCl buffer.

6. The process as claimed in claim 1 wherein said chromatography used in the purification step is hydrophobic interaction chromatography (HIC) Phenyl sepharose 6 fast flow.

7. The process as claimed in claim 1 wherein the diafiltration and concentration to obtain purified polysaccharides step is carried with 100 KDa PES membrane (0.1 m$^2$), with 6 to 8 volumes of Milli-Q water.

* * * * *